United States Patent
Rustad et al.

[11] Patent Number: 5,701,887
[45] Date of Patent: Dec. 30, 1997

[54] BREATHING CIRCUIT HEATING ELEMENT RETAINER

[75] Inventors: Andre M. Rustad, Etiwanda; Paul O. Davison, Costa Mesa, both of Calif.

[73] Assignee: Baxter International Inc., Deerfield, Ill.

[21] Appl. No.: 618,277

[22] Filed: Mar. 18, 1996

[51] Int. Cl.$^6$ ............................................. A61M 16/00
[52] U.S. Cl. ............................ 128/204.17; 128/204.18; 128/911
[58] Field of Search ............ 128/204.17, 200.24, 128/201.13, 201.16, 201.17, 203.26, 203.27, 204.18, 207.14, 203.16, 203.17, 202.27, 201.19, 911, 912, 200.26; 174/47, 99 R, 135; 600/139, 140, 141, 146

[56] References Cited

U.S. PATENT DOCUMENTS

| | | | |
|---|---|---|---|
| 4,967,744 | 11/1990 | Chua | 128/204.18 |
| 5,392,770 | 2/1995 | Clawson et al. | 128/203.77 |

*Primary Examiner*—Vincent Millin
*Assistant Examiner*—Robert N. Wieland

[57] ABSTRACT

In a breathing circuit such as a ventilator circuit, a heating element is used to provide improved temperature characteristics of the inspired air or breathing gas. An heating element retainer is disclosed which is operative to provide a central location of the heating element within the breathing circuit lumen.

8 Claims, 1 Drawing Sheet

BREATHING CIRCUIT HEATING ELEMENT RETAINER

FIELD OF THE INVENTION

The instant invention relates to ventilator breathing circuits and more specifically to heated breathing circuits.

BACKGROUND OF THE INVENTION

In a ventilator breathing circuit it is often necessary to heat incoming air to a patient so as to provide comfort and protection to the patient's pulmonary system. The introduction of oxygen or other gasses, due to expansive cooling of those gasses as they exit a tank, may cool the incoming breathing mixture to a point below that which is clinically desired for a specific patient. Additionally, it may be desirable in various clinical circumstances to provide breathing gas at an elevated temperature to the patient. For these and other reasons, breathing circuits are provided with heating wires so as to provide a constancy of the temperature of the breathing gas to a patient.

Previous embodiments of a breathing circuit wire retainer have been ¾ rings. These rings have a disadvantage as they are difficult to assemble into a breathing circuit and, therefore, increase the cost of the items. Furthermore, due to their shape, the retainers extant do not serve to hold the heating wire securely and, therefore, do not provide the constancy of temperature as is most desirable for the patient.

Furthermore, previous embodiments of a breathing circuit wire retainer have been designed in such a way that, to guarantee positive placement, knots are tied which can cause breakage. When knots are not used then wire migration can occur, since only one limb otherwise is fastened, which can give false airway temperature readings. These retainers have a disadvantage as they are also difficult to assemble into a breathing tube, therefore, increasing circuit cost.

U.S. Pat. No. 4,682,010 to Drapeau et al. discloses a breathing circuit having a heating wire placed in proximal relationship to the interior of a breathing circuit tube.

U.S. Pat. No. 4,967,744 to Chua discloses a breathing circuit having an inner support tube which supports a helically wound heating wire.

Both these embodiments are costly to manufacture and Drapeau, by heating the lumen from its periphery, preferentially heats the static boundary layer at the lumen periphery while allowing the breathing mixture in the tube center to pass through the lumen essentially unheated. Chua, while providing for more coaxial heating adds significant additional drag to the fluid flow in the tube by requiring two boundary layers—one about the lumen periphery and one about the central tube, in addition to providing a small internal diameter for the interior (feed) lumen.

SUMMARY OF THE INVENTION

It is a primary object of the invention to securely fasten both limbs of a heating wire in a breathing circuit.

It is another object to maintain a heating wire at a fixed distance from a temperature probe within the breathing circuit.

It is a further object of the invention to support the end of a heating wire in a central location in a breathing circuit lumen.

It is another object of the invention to provide an inexpensive means for supporting the heating element in a breathing circuit.

It is an additional object of the invention to provide for ease of assembly of a breathing circuit and heating element.

It is a further object of the invention to minimize drag in a breathing circuit by supporting a heating element in free air.

These and other objects of the instant invention will become apparent in the drawings, claims and detailed description of the preferred embodiment of the instant invention appended hereto.

DETAILED DESCRIPTION OF THE PREFERRED EMBODIMENT

Figure 1:
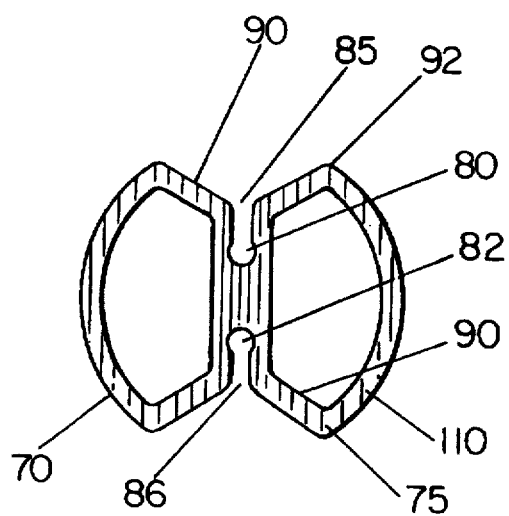
FIG. 1 is a plan view of the novel wire retainer.
Figure 2:
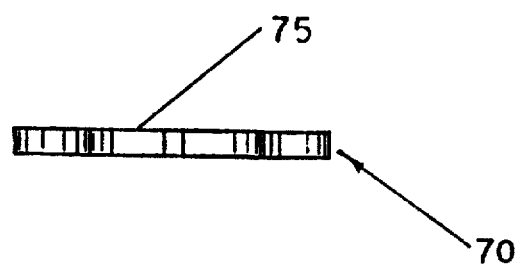
FIG. 2 is an edge view of the wire retainer.
Figure 3:
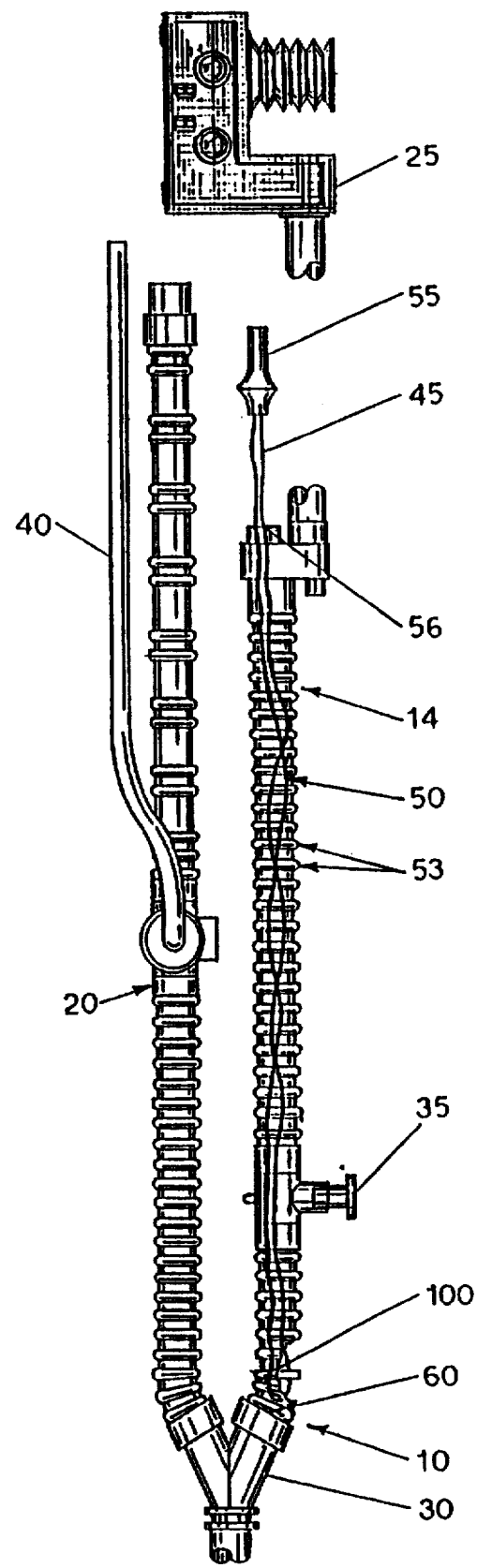
FIG. 3 is a cutaway view of the wire retainer as installed in a breathing circuit.

In a breathing circuit 10, having an input tube 15 and an output tube 20, air or breathing gasses are moved through the tubes by a ventilator 25 to a manifold 30. Various attachment points are appurtenant thereto and include such areas as a nebulizer port 35 and an exhalation valve drive line 40. The heating element 45 itself is supported within a lumen 50 defined within the input tube 15. The wire receives electricity from an external source via plug 55 located at the distal end 56 of inlet tube 15. In operation, a current passes through the element or wire 45 and heats the element by ohmic, or resistive, heating. At the proximal end 60 of the inlet tube 15, the heating wire 45 is supported by a wire retainer 70 which may be made of a thermoplastic material. Retainer 70 further includes a body 75 defining a plurality of wire ports 80, 82 wherein the ports 80, 82 are located radially outwardly from the central axis of the body 75. The body further defines transverse axial grooves 85, 86 which extend about a transverse axis from the aforementioned ports or groove termini 80, 82, wherein the grooves and ports act cooperatively to support and hold wire or element 45 in a central location in the lumen 50. The grooves 85, 86 are sized so as to present a smaller internal dimension than the ports 80, 82 so as to mechanically maintain wire 45 within the ports 80, 82 while providing for facile installation of the element 45 through the grooves 85, 86.

The retainer further comprises a plurality of radially extensive members 90 wherein the periphery of the members is substantially coextensive with the interior surface 100 of the lumen 50. Extending circumferentially from the distal ends 92 of the members 90 about the central axis of the body 75 are a plurality of lumen engaging supports 110 which are substantially circumferentially coextensive with the interior surface 100 at the lumen 50 which, in the present embodiment, displays a substantially figure-eight aspect as viewed face-on.

In operation, wire 45 is clipped to retainer 70 through grooves 85, 86 to rest in ports 80, 82, then retainer 70 is inserted into the proximal end 60 of lumen 50. The retainer 70 may be temporarily deformed to accomplish installation in lumen 50 until retainer 70 snaps into convolute area 53 and is thereby held centrally in lumen 50.

This embodiment, although presently preferred, is not intended to limit the scope of the invention as defined by the claims appended hereto.

In accordance with our invention, we claim:

1. In a breathing circuit having a tube, said tube defining a lumen, said lumen having an interior surface and a convolute section, and a heating element wire interior to said interior surface; a heating element retainer comprising a body having a plurality of ports defined therein and adapted to be inserted and retained in said convolute section and support said heating element wire by means of said plurality of ports defined within said body, said ports being further adapted to grip said element and hold same in a substantially fixed relationship with said body, and radially extensive deformable members extensive from said body with said members including deformable supports; said supports being substantially conterminous with said interior surface.

2. The invention according to claim 1 and said retainer being made of a thermo-plastic material.

3. The invention according to claim 1 and said body having a diameter less than, wherein said convolute area has a maximum diameter, said maximum diameter.

4. The invention according to claim 3 and said retainer adapted to hold a heating wire within said circuit and wherein said wire has a plurality of limbs, said retainer being further adapted to hold said plurality of limbs of said heating wire.

5. A method for effecting support of a heating wire in a breathing circuit having a convolute section comprising the following steps:

(1) wherein a heating wire retainer having a plurality of ports and said ports are adapted to retain said wire, threading said wire through said ports;

(2) wherein said retainer comprises a body having radially extensive deformable members extensive from said body and is adapted to fit within said convolute section, emplacing said retainer in said convolute section;

(3) drawing said wire through said breathing circuit and, wherein said circuit has a distal end, said drawing of said wire continuing to said distal end.

6. The invention according to claim 1 and said retainer further comprising a groove in said body extending radially outward from each port of said plurality of ports.

7. The invention according to claim 6 and said retainer further comprising said ports having a larger dimension than said grooves.

8. The invention according to claim 1 and said retainer further comprising said supports, in combination with said deformable members, having a substantially figure eight configuration.

* * * * *